United States Patent [19]

Annis et al.

[11] Patent Number: 4,857,041
[45] Date of Patent: Aug. 15, 1989

[54] URINARY INCONTINENCE PROSTHESES

[75] Inventors: David Annis, Bromborough; Malcolm C. Brown, Wirral; John R. Sutherst, Waterloo, all of England

[73] Assignee: National Research Development Corporation, London, England

[21] Appl. No.: 46,690

[22] Filed: May 7, 1987

[30] Foreign Application Priority Data

May 7, 1986 [GB] United Kingdom ............... 8611129

[51] Int. Cl.$^4$ ............................................. A61B 19/00
[52] U.S. Cl. ................................. 600/30; 128/DIG. 25
[58] Field of Search ............... 128/1 R, 630, DIG. 25, 128/830, 834, 836, 837; 604/367, 368, 370; 623/11, 12; 600/29, 30

[56] References Cited

U.S. PATENT DOCUMENTS

| 3,066,667 | 12/1962 | Berry | 128/DIG. 25 |
|---|---|---|---|
| 3,789,828 | 2/1974 | Schulte | 128/DIG. 25 |
| 3,862,452 | 1/1975 | Wichterle et al. | 623/12 |
| 4,019,498 | 4/1977 | Hawtrey et al. | 128/1 R |
| 4,457,299 | 7/1984 | Cornwell | 128/DIG. 25 |
| 4,497,074 | 2/1985 | Rey et al. | 623/12 |
| 4,570,629 | 2/1986 | Widra | 604/368 |
| 4,615,704 | 10/1986 | Frisch | 128/1 R |
| 4,636,213 | 1/1987 | Pakiam | 128/1 R |
| 4,657,553 | 4/1987 | Taylor | 623/66 |

OTHER PUBLICATIONS

"Intermittent Occlusion System" Timm et al., IEEE Trans. Biomed. Engin. 1970.

*Primary Examiner*—Max Hindenburg
*Attorney, Agent, or Firm*—Cushman, Darby & Cushman

[57] ABSTRACT

A prosthetic device (10) suitable for use in the treatment of stress incontinence in women by location as a cuff around the urethra, to elevate the bladder following prolapse, comprises a body (11) composed predominantly of a cross-linked synthetic polymer hydrogel having a water content of the order of 90%, and preferably about 95%, by weight. The hydrogel can be homogeneous through the body but in this event the body suitably has a local reinforcement (12), such as by embedded plastics material mesh, in at least one relatively small edge portion to enhance its tear resistance in relation to sutures (13) passed therethrough. The body is suitably of kidney shape having dimensional proportions of approximately 5×3×1. cms.

3 Claims, 1 Drawing Sheet

URINARY INCONTINENCE PROSTHESES

This invention concerns urinary incontinence prostheses and more particularly such prostheses for application in the treatment of stress incontinence in women.

BACKGROUND OF THE INVENTION

The normal control over the passage of urine is thought to be achieved by two mechanisms. One such mechanism involves the sphincter muscular action which affects the lower part of the tubular outlet of the bladder normally to provide a steady tonic contraction at rest and an increased contraction during coughing, lifting or other stress when the pressure in the abdominal cavity rises. The second mechanism involves the transmission of abdominal pressure to the proximal part of the outlet of the bladder, the urethra, enabling the pressure acting on the urethra from without the same to rise correspondingly with that acting on the urethra from within by way of the bladder when stressed.

This second mechanism requires that the upper part of the urethra be located within the abdominal pressure zone and, in women, this is above the muscles of the floor of the pelvis. It follows that loss of this mechanism is commonly associated with prolapse such that the female urethra is lowered from the pressure zone, with a consequent incidence of stress incontinence.

Different proposals have been made for treatment of this last condition, but none appears fully satisfactory.

Surgical treatment normally involves elevation of the base of the bladder to restore a normal location for the urethra. Commonly performed operations are urethroplasty, in which the urethra is buttressed from below, and coposuspension, in which structures surrounding the urethra are sutured to ligaments above it in the pelvis. Another deploys a sling construction. All of them can lead to urethral scarring which may adversely affect normal function.

A subsequently proposed treatment involves the use of a pedicle graft of fat taken from an adjacent site and placed wholly or partly as a cuff around the urethra to restore its mobility and flexibility. Unfortunately the fat tends to disappear with time.

Other treatments involve the use of mechanical aids, such as a hydraulically inflatable urethral cuff or a vaginal inflatable pessary, or synthetic materials such as polyethylene gauze, but these can prove unsatisfactory by way of mechanical failure, discomfort, foreign body reaction, and other eventualities.

SUMMARY OF THE INVENTION

An object of the present invention is to improve the prospects for satisfactory treatment of stress incontinence in women by following the principle of the above-mentioned pedicle graft approach, but with the use of an alternative composition to fat for the cuff.

To this end the present invention provides, according to one aspect thereof, the use, in the treatment of urinary stress incontinence in women, of a body composed predominantly of a cross-linked synthetic polymer hydrogel having a water content of the order of 90% by weight.

In another aspect the invention provides a prosthetic incontinence device comprising such a body.

The choice of the specified composition for the body has been made to provide, as far as possible, those properties considered to be appropriate for the related prosthetic role.

In this connection it is considered that the physical properties should not differ markedly from those of the natural tissues which will be adjacent to the body when in use. More particularly the body should be of a similar compliance to the tissues so as not to damage the latter, while at the same time having adequate stability to allow manipulation during surgery and to sustain its function thereafter. Also the physical properties should be such that the material will transmit intra-abdominal pressure changes promptly and without significant attenuation. In addition the body should allow sterilisation by an acceptable technique.

The body should also be biocompatible when inuse. In this connection the body should be biopassive to the extent that it is not dispersed, like fat, nor should it be associated with any other adverse reaction. However it is appropriate that the body should promote or be susceptible to the formation of loose connective tissue over its surface to provide an encapsulating attachment with the adjacent tissues, which growth does not of itself alter the desired physical properties.

In development of the invention to date various cross-linked synthetic polymer hydrogels have been made which can provide most of the desired properties, but the specified water content has proved to be effectively critical in respect of pressure transmission and encapsulation. Water content of a lesser order is associated with a stiffness which adversely attenuates pressure transmitting capability. In fact the specified water content is preferably about 95%.

However, this development also shows that a body of homogeneous composition at the specified water content has an inadequate tear resistance for the purposes of its securement by sutures during surgery. This deficiency has been resolved in a presently preferred form of the invention by the provision of localised reinforcement at appropriate edge portions of the body, typically by embedding plastics material mesh in the hydrogel during its preparation. It is to be noted that overall reinforcement is inappropriate to attainment of the desired pressure transmission capability.

In order to clarify the invention further, the same will now be described by way of example with reference to the accompanying drawings, in which:

DESCRIPTION OF THE PREFERRED EMBODIMENTS

Figure 1:
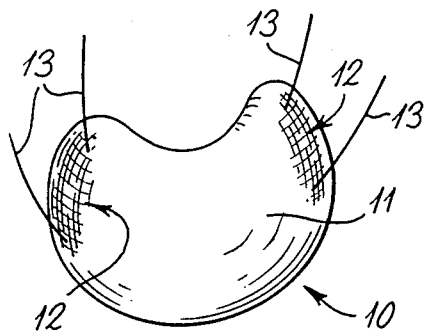
FIG. 1 diagrammatically illustrates a preferred form of device according to the invention, and FIGS. 2, 3 and 4 schematically illustrate alternative surgical procedures for the use of the device of FIG. 1.

The device of FIG. 1 is denoted generally at 10 and comprises a body 11 of cross-linked synthetic polymer hydrogel of kidney shape typically measuring approximately 5×3×1 cms, although it may be appropriate to provide other sizes with similar proportions.

The hydrogel of the body 11 is of homogeneous form with a water content of about 95% by weight. Suitable hydrogels have been made by modification of the method employed to produce poly(acrylamide) hydrogels from acrylamide water solutions. More specifically the modified method involves cross-linking with small amounts, typically 0.1% by weight, of methylene bisacrylamide and thermal initiation with ammonium persulphate at about 1% by weight.

In order to enhance the tear resistance of the body 11 for the purposes of securement by sutures, pledgets 12 of polypropylene mesh reinforcement are embedded in the longitudinal end portions of the body during its preparation. Sutures 13 passing through the reinforced portions of the body can also be inbuilt during preparation of the body.

The resultant device is sterilisable by autoclaving.

Turning to the question of use of the device: this is to involve location as a cuff extending wholly or partly around the proximal urethra to elevate the same from the pelvic floor and thereby restore its capability for response to intraabdominal pressure as indicated earlier above. It is proposed in practice that such location be effected by way of the vagina by opening the anterior vaginal wall longitudinally and separating vaginal tissue from the bladder and urethra to allow access to the desired site. When the site is exposed, the device can be located and its sutures used to tether the device to adjacent para-urethral tissues, or by carrying the sutures upwards retropublically on a long needle to the anterior abdominal wall for tethering to the pelvic ligaments, for example the pectineal ligament, or to the rectus sheath. The latter options are likely to provide stronger support for the device without undue added complication to the surgery, there being an additional need for small abdominal incisions in this case to locate and secure the suture ends.

Figure 2:
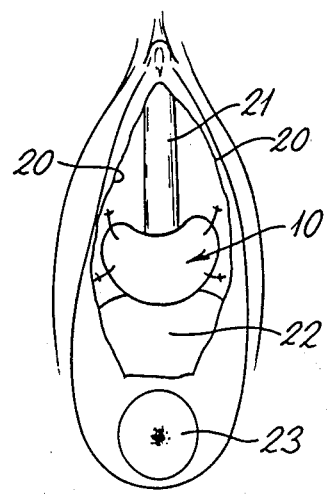
Figure 3:
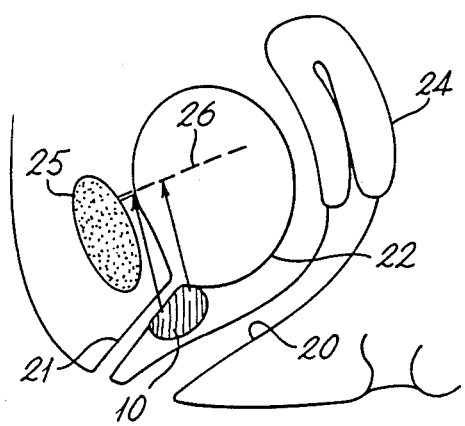
Figure 4:
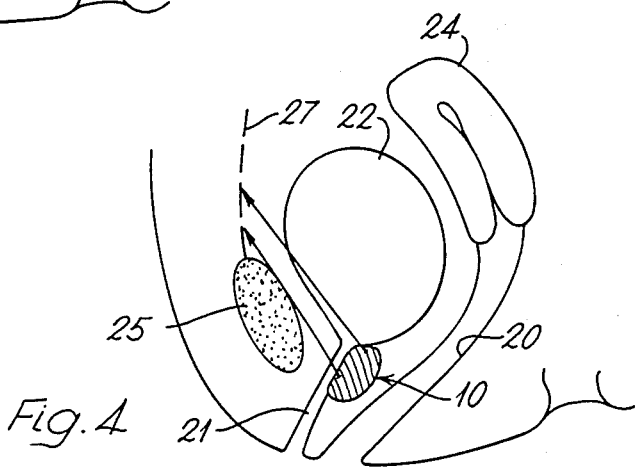

These surgical procedures are respectively illustrated by FIGS. 2, 3 and 4 in which the vagina and, in the first procedure, its cut wall are denoted at 20, and the urethra, bladder, cervix, uterus, pubic bone, pectineal ligament and rectus sheath are respectively denoted at 21 to 27.

While the invention has been described with particular reference to presently preferred forms, other possibilities exist within the scope of the invention as defined in the appended claims. For example, it has been contemplated that all of the properties discussed above may, with further hydrogel development, be attained without need for such reinforcement. More specifically, one such possibility for development is the provision of a body having a core around which is grafted an outer layer of hydrogel of 90% water content, the core also being hydrogel material of a lesser order of water content affording all of the desired properties except that for ingrowth. Also, an alternative to securement by sutures can involve the use of adhesive, such as of cyanoacrylate form, to bond the ends of the device together into a closed cuff configuration.

We claim:

1. A method of treating female urinary incontinence occurring due to prolapse of the bladder, comprising:
   elevating the bladder from the pelvic floor by locating adjacent to the proximal urethra below the bladder a body composed predominantly of cross-linked synthetic polymer hydrogel material having a water content of the order of 90% by weight at least over the exterior surface of said body.

2. The method according to claim 1 which comprises locating said body as a cuff which at least partly embraces the urethra, and tethering said body with sutures to the adjacent para-urethral tissues.

3. The method according to claim 1 which comprises locating said body as a cuff which at least partly embraces the urethra, and tethering said body with sutures to at least one of the pelvic ligaments or the rectal sheath.

* * * * *